(12) United States Patent
Schmieding

(10) Patent No.: US 6,616,674 B2
(45) Date of Patent: Sep. 9, 2003

(54) NOTCHED SUTURE HOOK

(75) Inventor: Reinhold Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 09/803,617

(22) Filed: Mar. 9, 2001

(65) Prior Publication Data

US 2001/0037119 A1 Nov. 1, 2001

Related U.S. Application Data

(60) Provisional application No. 60/189,152, filed on Mar. 14, 2000.

(51) Int. Cl.$^7$ ................................................ A61B 17/10
(52) U.S. Cl. ........................................... 606/139; 606/1
(58) Field of Search ................. 606/139, 112, 606/222, 223, 224, 1

(56) References Cited

U.S. PATENT DOCUMENTS

| | | | | |
|---|---|---|---|---|
| 5,501,692 A | * | 3/1996 | Riza | 606/148 |
| 5,643,292 A | * | 7/1997 | Hart | 606/144 |
| 5,653,716 A | * | 8/1997 | Malo et al. | 606/139 |
| 5,827,291 A | * | 10/1998 | Fucci et al. | 606/104 |
| 6,096,041 A | * | 8/2000 | Gellman et al. | 606/72 |
| 6,099,538 A | * | 8/2000 | Mosses et al. | 606/144 |
| 6,283,979 B1 | * | 9/2001 | Mers Kelly et al. | 606/139 |
| 6,464,271 B1 | * | 10/2002 | Irvin, Jr. | 294/26 |

* cited by examiner

Primary Examiner—Henry Bennett
Assistant Examiner—Nihir Patel
(74) Attorney, Agent, or Firm—Dickstein Shapiro Morin & Oshinsky, LLP

(57) ABSTRACT

A suture hook for use in arthroscopic repairs of the shoulder has a tapered shaft and a handle disposed on the proximal end of the shaft. An O-ring post for holding suture is disposed on the handle. A curved hook on the distal end of the shaft terminates in a sharp point for piercing tissue. A slot is formed distally on the convex side of the hook for receiving a loop of the suture. A length of suture loaded as a loop onto the suture anchor is held in the slot and secured by wrapping the suture tails around the O-ring post. The loaded suture hook is advanced through tissue by piercing the tissue with the sharp tip. The suture is then released from the post and the hook is retrograded leaving the loop of suture available for further surgical manipulation.

14 Claims, 2 Drawing Sheets

NOTCHED SUTURE HOOK

This application claims the benefit of U.S. Provisional Application Serial No. 60/189,152, filed Mar. 14, 2000.

BACKGROUND

1. Field of the Invention

The present invention relates to a suture hook for use in orthopaedic surgery. More specifically, the present invention relates to a notched suture hook for passing surgical suture through tissue.

2. Brief Description of the Related Art

It is desirable to attach suture to tissue in connection with arthroscopic surgical repair of torn tissue or reattachment of tissue to bone. Instruments have been developed for retrieving suture. It would be desirable to have an instrument capable of passing a loop of suture through tissue.

SUMMARY OF THE INVENTION

The suture hook of the present invention provides a simple and efficient instrument for passing a loop of braided suture through single or multiple tissue layers. The instrument preferably is used for side-to-side repair of the rotator cuff, capsular application and closure of the rotator interval.

According to a preferred embodiment, the suture hook has a shaft with a proximal end and a distal end. A handle is disposed on the proximal end of the shaft. A suture retaining device is disposed on the handle, preferably in the form of an O-ring post. Two strands of No. 2 braided polyester suture wrapped in tandem under the O-ring post are held securely. A curved or bent hook is disposed on the distal end of the shaft. A distal tip of the hook terminates in a sharp point. A slot is formed on the hook for receiving suture, preferably in the form of a cut made perpendicular to the axis of the shaft in the convex side of the hook. The suture hook of the present invention is provided in straight, curved right, or curved left versions.

In a preferred method of using the invention, the slot in the tip of the instrument is loaded with a loop of No. 2 braided suture. The tails of the suture are secured around the suture post disposed on the handle. The pointed tip of the hook is used to pierce tissue and advance the suture loop captured in the slot through the pierced tissue.

The suture loop then is easily retrieved. The suture hook of the present invention can be used as a suture shuttle to pass anchor sutures through tissue. Particularly preferred applications include Bankart and rotator cuff repairs.

Other features and advantages of the present invention will become apparent from the following description of the invention which refers to the accompanying drawings.

DETAILED DESCRIPTION OF THE PREFERRED EMBODIMENTS

Figure 1:
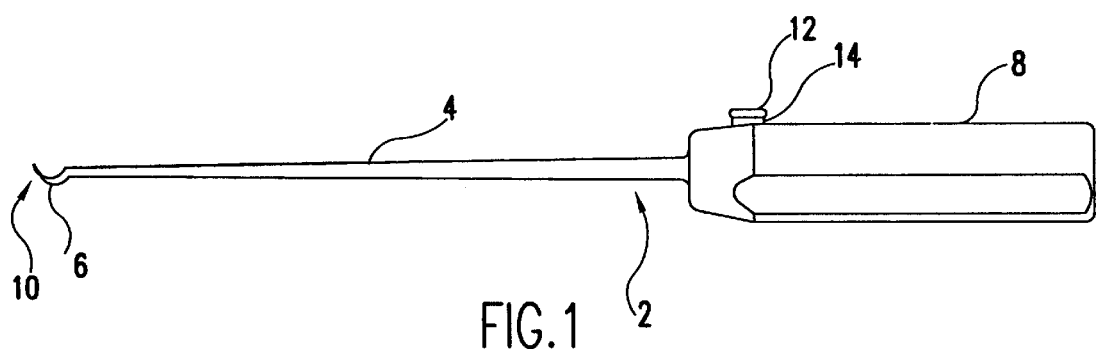
FIG. 1 is an elevation view of a slotted suture hook according to the present invention.

Referring initially to FIG. 1, a straight slotted suture hook 2 according to the present invention is shown in elevation. The suture hook includes a round tapered shaft 4 made of stainless steel. A curved hook 6 is formed on the distal end of the shaft. The shaft terminates in a sharp point for piercing tissue. A handle 8 is provided on the proximal end of the shaft and manufactured from aluminum.

Hook 6 is provided with a slot 10 for receiving suture. The slot is formed on the outer convex surface of the hook toward the sharp distal tip of the shaft. The slot is formed by cutting the hook perpendicular to the axis of the shaft. The slot is sized to hold a no. 2 suture.

Handle 8 is provided with a capped post 12 around which a No. 2 O-ring 14 is disposed. The O-ring post combination is provided to hold securely two strands of No. 2 braided polyester suture wrapped in tandem under the O-ring. The post fits into a hole formed in the handle. During assembly, shaft 4 is fitted into a socket in handle 8. A hole through the shaft aligns with the hole in the handle. The shaft is secured to the handle by inserting the post 12 in press fit fashion into the respective holes in the handle and the shaft.

Figure 2:
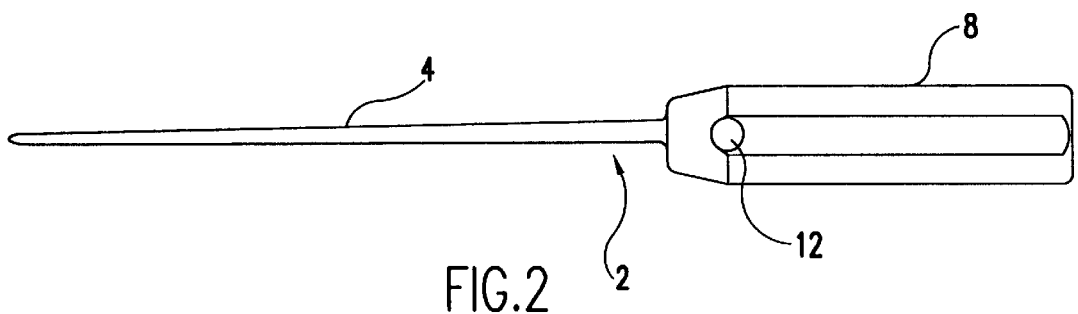
FIG. 2 is a plan view of a straight slotted suture hook according to the present invention.
Figure 3:
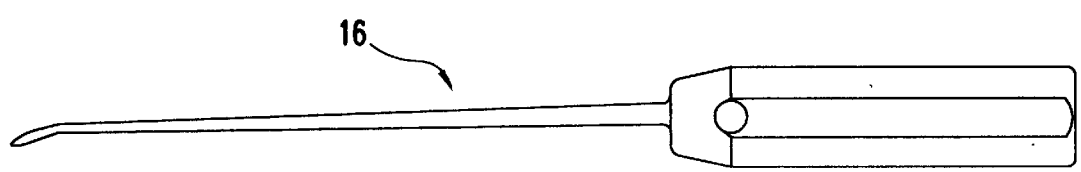
FIG. 3 is a plan view of a left curved slotted suture hook according to the present invention.
Figure 4:
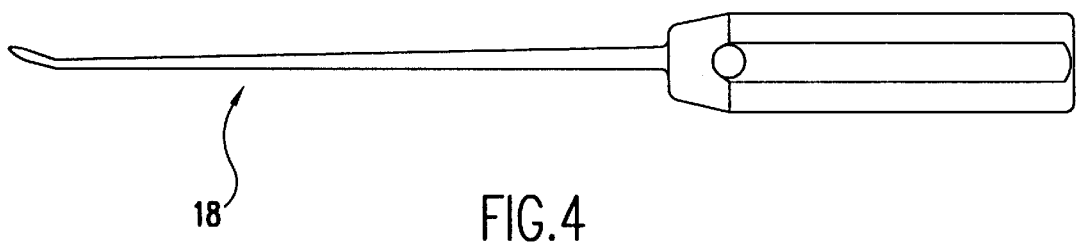
FIG. 4 is a plan view of a right curved slotted suture hook according to the present invention.

Referring to FIG. 2, a plan view of suture hook 2 shows that hook 6 is axially aligned with shaft 4. FIGS. 3 and 4 illustrate a left slant suture hook 16 and a right slant suture hook 18, respectively. The hook is slanted approximately 15–20° from the longitudinal axis of shaft 4. In all other respects, suture hooks 16 and 18 are substantially similar to suture hook 2. In all three embodiments of the suture hook, the hook is sized to pass through a 7 mm×7 cm cannula.

Figure 5:
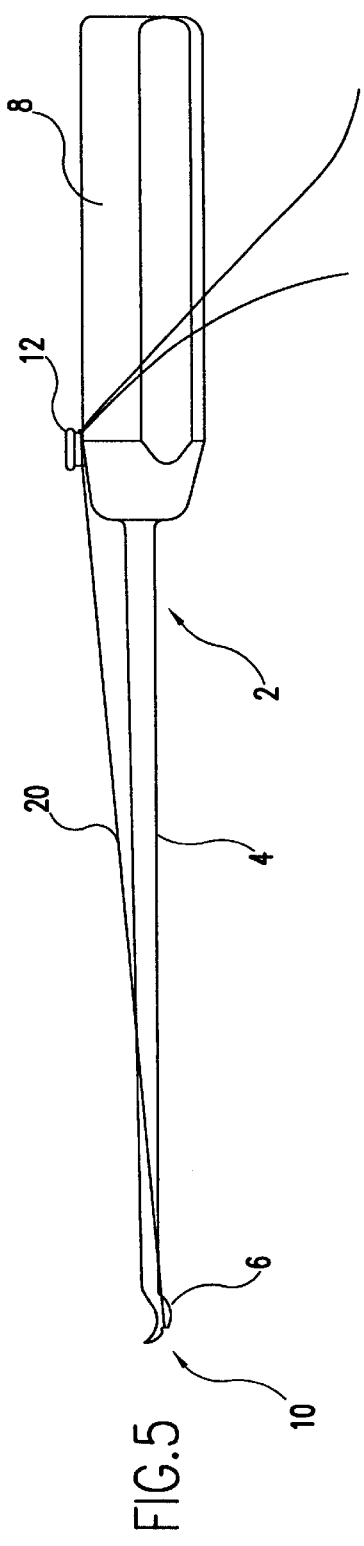
FIG. 5 is an elevation view of the suture hook of FIG. 1 loaded with a length of suture according to the present invention.
Figure 6:
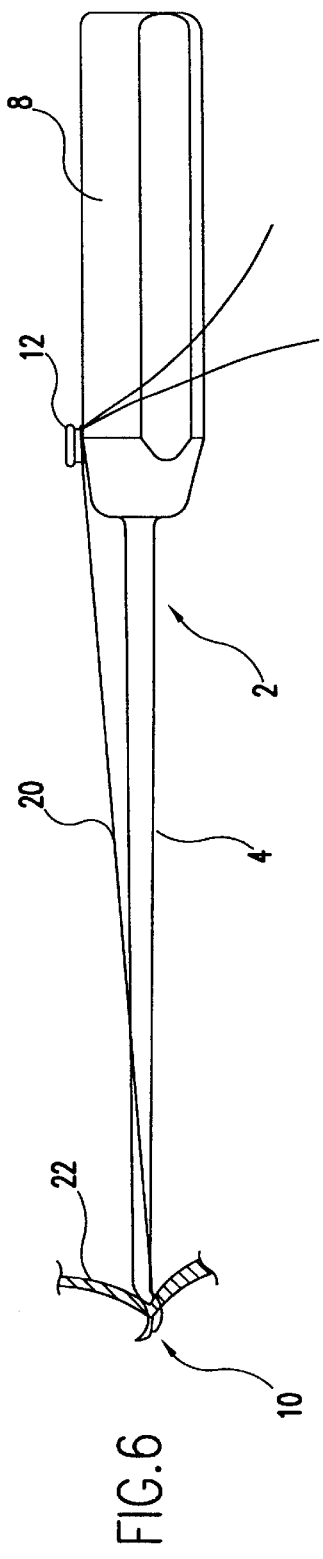
FIG. 6 is a schematic illustration of a step of piercing tissue with the loaded surgical hook of FIG. 5 in an arthroscopic surgical procedure according to the present invention.
Figure 7:
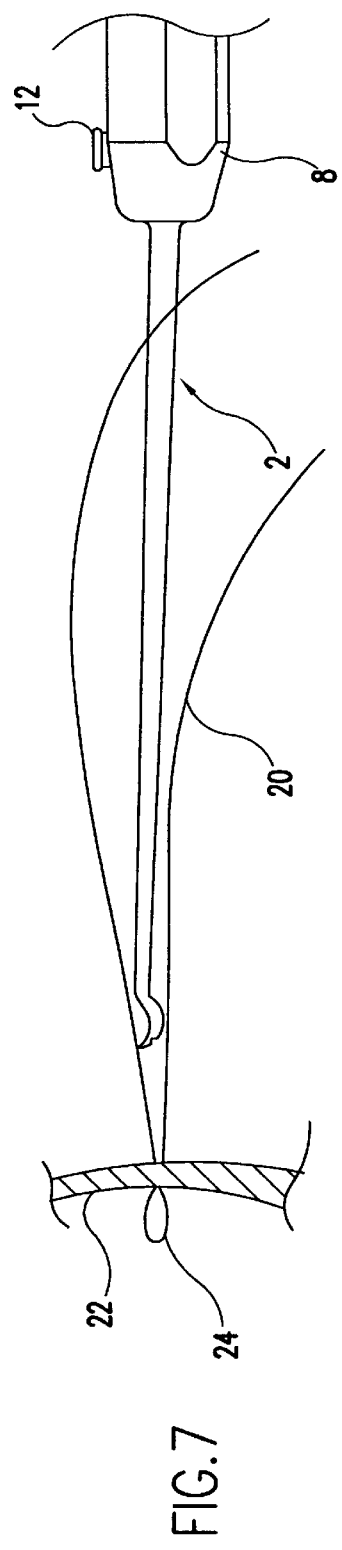
FIG. 7 is a schematic illustration of a step of retrograding the surgical hook of FIG. 5 in an arthroscopic surgical procedure according to the present invention.

FIGS. 5–7 illustrate a method of using suture hook 2 to advance a loop of suture through tissue during arthroscopic surgery. Initially, a length of suture 20 is loaded on the suture hook as shown in FIG. 5. The suture is looped around the distal end of the suture hook, the apex of the loop being captured in slot 10. The suture is secured by wrapping the tails of the suture in tandem around post 12 under O-ring 14.

The loaded suture hook is then advanced by the surgeon through a cannula toward a section of tissue 22 involved in arthroscopic repair of the shoulder, for example. As shown schematically in FIG. 6, the pointed distal tip of hook 6 pierces the tissue and advances the suture captured in slot 10. Once the suture has been advanced through the tissue 22, the tails of the suture are unwrapped from post 12, and the suture hook is retrograded. Referring to FIG. 7, removing the suture hook leaves a loop of suture 24 remaining proud on the distal side of the tissue. The suture loop 24 then can be further manipulated as necessary to implement the tissue repair.

Although the present invention has been described in relation to particular embodiments thereof, many other variations and modifications and other uses will become apparent to those skilled in the art. The present invention, therefore, is to be limited not by the specific disclosure herein, but only by the appended claims.

What is claimed is:

1. A suture hook comprising:
    a shaft having a proximal end and a distal end;
    a handle disposed on the proximal end of the shaft;
    a suture retainer disposed on the handle, the suture retainer comprising an O-ring post disposed on a top side of the handle;

a hook disposed on the distal end of the shaft, a distal tip of the hook terminating in a sharp point; and a slot formed on the hook for receiving suture.

2. The suture hook of claim 1, wherein the slot is formed in a convex side of the hook.

3. The suture hook of claim 2, wherein the slot is formed distally of the convex side of the hook.

4. The suture hook of claim 1, wherein the hook is curved.

5. The suture hook of claim 1, wherein the hook slants away from a longitudinal axis of the shaft.

6. The suture hook of claim 1, wherein the hook opens upwardly.

7. The suture hook of claim 1, wherein the hook is aligned axially with the shaft.

8. A suture hook consisting essentially of:

a straight shaft having a proximal end and a distal end;

a handle disposed on the proximal end of the shaft;

an O-ring post for holding suture disposed on the handle;

a curved hook disposed on the distal end of the shaft, a distal tip of the hook terminating in a sharp point for piercing tissue; and a slot formed distally on a convex side of the hook for receiving a loop of the suture.

9. The suture hook of claim 8, wherein the slot is cut into the hook perpendicularly to an axis of the shaft.

10. A method of performing arthroscopic surgery using a suture hook having a shaft with a proximal end and a distal end, a handle disposed on the proximal end of the shaft, an O-ring post disposed on the handle, a hook disposed on the distal end of the shaft, a distal end of the hook terminating in a sharp point, and a slot formed on the hook, the method comprising the steps of:

loading a length of suture into the slot formed on the hook, the length of suture forming a loop having two free tails; and securing the free tails of the suture to the O-ring post.

11. The method of claim 10, further comprising the step of inserting the suture through tissue by piercing the tissue with the pointed distal tip of the hook.

12. The method of claim 10, wherein the arthroscopic surgery is performed in a human shoulder.

13. The method of claim 12, wherein the arthroscopic surgery is one of Bankart and rotator cuff repair.

14. The method of claim 12, wherein the arthroscopic surgery is selected from the group consisting of side-to-side repair of rotator cuff, capsular plication, and closure of rotator interval.

* * * * *